(12) United States Patent
Walker et al.

(10) Patent No.: US 9,492,546 B2
(45) Date of Patent: Nov. 15, 2016

(54) USE OF BETHANECHOL FOR TREATMENT OF XEROSTOMIA

(75) Inventors: Ian Walker, Harston Cambridgeshire (GB); Michael Frodsham, Flintshire (GB)

(73) Assignee: Acacia Pharma Limited, Cambridgeshire (GB)

( * ) Notice: Subject to any disclaimer, the term of this patent is extended or adjusted under 35 U.S.C. 154(b) by 0 days.

(21) Appl. No.: 14/115,816

(22) PCT Filed: May 4, 2012

(86) PCT No.: PCT/GB2012/050976
§ 371 (c)(1),
(2), (4) Date: Feb. 11, 2014

(87) PCT Pub. No.: WO2012/153110
PCT Pub. Date: Nov. 15, 2012

(65) Prior Publication Data
US 2014/0187629 A1 Jul. 3, 2014

(30) Foreign Application Priority Data
May 6, 2011 (GB) .................................. 1107533.0

(51) Int. Cl.
| | | |
|---|---|---|
| A61K 31/27 | (2006.01) | |
| A61K 47/22 | (2006.01) | |
| A61K 31/37 | (2006.01) | |
| A61K 9/00 | (2006.01) | |
| A61K 9/08 | (2006.01) | |

(52) U.S. Cl.
CPC .............. *A61K 47/22* (2013.01); *A61K 9/006* (2013.01); *A61K 9/08* (2013.01); *A61K 31/27* (2013.01); *A61K 31/37* (2013.01)

(58) Field of Classification Search
CPC ....... A61K 31/27; A61K 47/02; A61K 9/006
USPC ....................................................... 514/478
See application file for complete search history.

(56) References Cited

U.S. PATENT DOCUMENTS

| 5,340,821 A | 8/1994 | Abe et al. |
| 2008/0317679 A1 | 12/2008 | Tamarkin et al. |
| 2012/0232137 A1 | 9/2012 | Cooper et al. |

FOREIGN PATENT DOCUMENTS

| WO | WO 9715296 A1 | 5/1997 |
| WO | WO-9809623 A2 | 3/1998 |
| WO | WO-9836733 A2 | 8/1998 |
| WO | WO-2007092811 A2 | 8/2007 |
| WO | WO 2008100434 A1 | 8/2008 |
| WO | WO-2011058366 A1 | 5/2011 |
| ZA | 9610154 A | 6/1997 |

OTHER PUBLICATIONS

Allen. "Bethanechol 5-mg/mL Oral Liquid." *Int. J. Pharmaceut. Compound.* 9.6(2005):473.
Chainani-Wu et al. "Assessment of the Use of Sialogogues in the Clinical Management of Patients with Xerostomia." *Spec. Care Dentist.* 26.4(2006):164-170.
Epstein et al. "A Clinical Trial of Bethanechol in Patients with Xerostomia after Radiation Therapy. A Pilot Study." *Oral Surg. Oral Med. Oral Pathol.* 77.6(1994):610-614.
Hodosh et al. "Treatment of Aphthous Stomatitis with Saturated Potassium Nitrate/Dimethyl Isosorbide." *Quintessence Int.* 35.2(2004):137-141.
Jham et al. "A Randomized Phase III Prospective Trial of Bethanechol to Prevent Radiotherapy-Induced Salivary Gland Damage in Patients with Head and Neck Cancer." *Oral Oncol.* 43.2(2007):137-142.
Ekstrom et al. "Secretion From Submucosal Salivary Glands of the Ferret in Response to a Cholinesterase Inhibitor Applied onto the Oral Mucosa." *Eur. J. Oral Sci.* 11 0.3(2002):230-236.
Kimura et al. "Relationship Between Nasal Absorption and Physicochemical Properties of Quaternary Ammonium Compounds." *Arch. Int. Pharmacodyn.* 31 0(1991):13-21.
Restrepo. "Use of Inhaled Anticholinergic Agents in Obstructive Airway Disease." *Respir. Care.* 52.7(2007):833-851.
Smart, J.D., "Buccal Drug Delivery," *Expert Opin. Drug Deliv.*, 2005, vol. 2, No. 3, pp. 507-517.

*Primary Examiner* — Raymond Henley, III
(74) *Attorney, Agent, or Firm* — Cooley LLP; Ivor R. Elrifi; Heidi A. Erlacher

(57) ABSTRACT

A formulation for topical administration, comprises bethanechol and a penetration enhancer. The formulation is preferably used by being maintained in the buccal cavity for a period of time prior to being swallowed.

19 Claims, 2 Drawing Sheets

USE OF BETHANECHOL FOR TREATMENT OF XEROSTOMIA

RELATED APPLICATIONS

This application is a national stage application, filed under 35 U.S.C. §371, of International Application No. PCT/GB2012/050976, filed May 4, 2012, which claims benefit of priority from GB Application No. 1107533.0, filed May 6, 2011.

FIELD OF THE INVENTION

This invention relates to a formulation of bethanechol that is intended for use in the treatment of salivary gland dysfunction by topical application to the oral mucosa.

BACKGROUND OF THE INVENTION

Xerostomia can be defined as the subjective sensation of dryness of the mouth. This is usually the result of a decrease in the volume of saliva secreted but may also be due to a change in composition of saliva. The most common cause for salivary gland hypofunction is drug treatment; another cause is Sjogren's syndrome.

Xerostomia is an important condition in cancer patients. In head and neck cancer patients, xerostomia arises from collateral radiation damage to the salivary glands. Xerostomia is also a problem in the broader cancer population. These patients suffer xerostomia principally as a result of the medications, e.g. cytotoxic chemotherapy agents, that they receive.

A number of pharmacological agents have been used as salivary stimulants, including yohimbine and nicotinamide. The most widely used are parasympathomimetic drugs, choline esters or anticholinesterase drugs. The most well known is pilocarpine which acts primarily on muscarinic receptors. Muscarinic agonists, when administered systemically, tend to produce side-effects including sweating and cardiovascular changes.

Bethanechol chloride, also called carbamyl-methylcholine chloride, is a known drug which has been used clinically for many years. It is available in tablets and as an injection, and is used as a stimulant of the smooth muscle of the gastrointestinal tract, and in particular the urinary bladder.

Bethanechol administered orally has been tested in the treatment of xerostomia in a small number of clinical studies. The drug has been reported to increase salivary flow. Available data suggest that effects on salivation are dose-related, up to the maximum dose which may be safely administered via the oral route. In one study in patients with head and neck cancer-associated xerostomia, it was reported that of a total of 55 patients who were considered for enrolment, 12 (22%) were not eligible to take oral bethanechol due to systemic conditions (Jham et al. 2007, Oral Oncol. 43:137-142).

One potential way to increase efficacy and yet avoid further side-effects could be to give drugs by topical application to the oral mucosa, in order to directly target the underlying minor salivary glands. For this to work the drug must be able to cross the oral mucosal membrane. The concept of buccal drug delivery is well known and a number of reviews on the subject have been published; see for example Buccal Drug Delivery by John Smart (2005), Expert Opin. Drug Deliv., 2(3):507-517. The abstract of this article states that "The buccal mucosa, however, while avoiding first pass effects is a formidable barrier to drug absorption". And later "Currently this route is restricted to the delivery of a limited number of small lipophilic molecules that readily cross the buccal mucosa". In general, drug permeability across buccal tissue is dependent upon physicochemical properties of the drug, such as lipophilicity, molecular weight, and degree of ionisation at physiological pH. There are two possible route of absorption through the squamous stratified epithelium of the oral mucosa, these being transcellular (intracellular, passing through the cell) and paracellular (intercellular, passing around the cell). Permeation has been reported to be mainly by the paracellular route, through the intracellular lipids produced by membrane-coating granules; however, the route taken depends upon the physicochemical properties of the drug. Generally small molecules that are predominantly lipophilic, with a Log P range of 1.6-3.3, are absorbed most rapidly, and most drugs delivered successfully via the buccal or sublingual route are lipophilic. A compound with a Log P value of less than 0 or less than 1 is usually considered too hydrophilic to be a drug candidate, particularly if it needs to cross lipophilic biological membranes for its activity.

Chemically, bethanechol chloride is a quaternary ammonium compound. It is very polar in nature and has a high aqueous solubility (hydrophilic) and a calculated log P value of around −4.0. This is one of the lowest values reported in the literature for a clinically used pharmaceutical agent. Consistent with these physicochemical properties, bethanechol does not significantly penetrate into the CNS at therapeutic doses and is only poorly absorbed from the GI tract.

WO2011/058366 (published 19 May 2011, after the priority date claimed in connection with the present specification) discloses the use, preferably in man, when administered locally to the oral mucosa, of bethanechol, e.g. as the chloride, for the treatment of xerostomia. When so administered in certain formulations, and even at doses below those known to be associated with side-effects when administered orally, bethanechol chloride is unexpectedly found to be an effective treatment of the condition. This is especially surprising, given that the physicochemical properties of bethanechol chloride are such that it is very difficult to consider using the drug for topical applications where passage of the drug across mucosal membranes would be required for activity. This is particularly the case for topical use in the treatment of xerostomia, whereby penetration of bethanechol across buccal mucosal membrane would be required for the drug to reach underlying salivary glands.

SUMMARY OF THE INVENTION

According to the present invention, a novel formulation is of a type suitable for topical administration, e.g. a liquid or semi-solid formulation, comprising bethanechol and a penetration enhancer.

WO2011/058366 discloses Preclinical and Clinical Studies showing the utility of bethanechol in the treatment of xerostomia. As reported below, enhanced results are obtained by the inclusion of a skin penetration enhancer.

DESCRIPTION OF THE INVENTION

Figure 1:
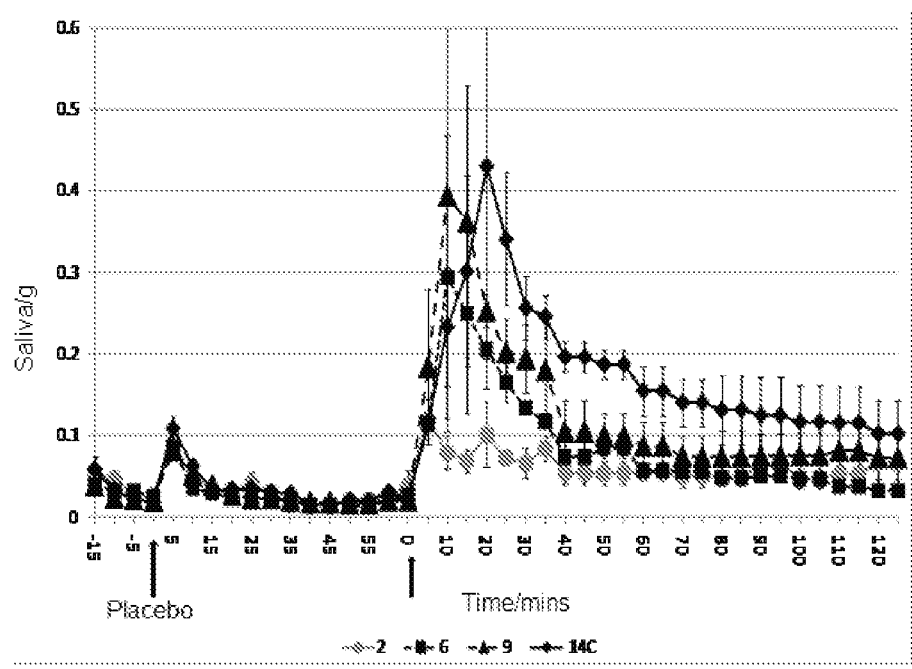
FIG. 1 is a plot of saliva/g versus time (mins).

The penetration enhancer that is used in the present invention is typically dimethyl isosorbide. The amount of penetration enhancer that is used is typically chosen with a view to get an increased amount of bethanechol across the buccal mucosa, and sufficient to provide efficacy, but also to avoid the risk of side-effects. The amount is preferably 5 to 40% w/w of the formulation.

For the purpose of the present invention, bethanechol is typically administered via the buccal route with the intention of providing a direct action on the salivary glands, thus resulting in an improvement of conditions associated with xerostomia. In one embodiment of the invention, the administered dose of bethanechol is held within the buccal cavity for a specified period of time in order to facilitate a local action on the minor salivary glands. The buccal contents are then swallowed such that any drug not absorbed through the buccal mucosa has the opportunity to gain entry to the systemic circulation via gastrointestinal absorption, and this achieves a secondary stimulation of salivary flow including from the major glands. The period of time that the formulation is held in the mouth before swallowing may be from 30 seconds to 5 minutes, preferably 1 to 3 minutes, more preferably 2 minutes.

A formulation of the invention is typically in a single unit dose form. It may be packaged as, e.g. a sachet, vial, blow-fill seal container, multidose container with separate doses administered manually, for example using a syringe, multidose container with unit dose dispenser, e.g. unidose pump or spray, semi-solid in tube, from which an appropriate amount can be extruded. The formulation is preferably "clean", i.e. meets the European Pharmacopeia microbiological requirements for oromucosal products and aqueous preparations for oral administration. There is no need for a preservative in the formulation if it is provided in a container for single-use. In multi-dose containers, the formulation preferably comprises a self-preserving system (e.g. ethanol or other alcohol) and/or includes an appropriate preservative.

Other suitable ingredients in a formulation of the invention include those of the type given under "Function" in Table 1, below. One such additive is a viscosity modifier, since it is desirable that the formulation is sufficiently viscous to be retained on the mucosa but not so viscous that it is difficult to administer or spread over the mucosa or retard drug release from the formulation.

When it is intended that the bethanechol is swallowed after a residence time in the buccal cavity, the dosing volume for a liquid or semi solid formulation is typically between 0.1 ml and 1.0 ml, preferably 0.25 ml to 0.75 ml, more preferably 0.3 ml to 0.6 ml.

In order to facilitate the bethanechol reaching the minor salivary glands, the bethanechol may be present in the formulation as a saturated solution. Alternatively, it may be a sub-saturated solution.

There is a range of delivery systems for delivery of drugs to the buccal mucosa (see Smart (2005), supra; this reference is incorporated herein by reference, in its entirety). These include buccal bioadhesive systems which may be tablets, patches, films, semisolids, liquids and particulates. Semi-solid formulations include gels and ointments. Appropriate dosage levels may be determined by any suitable method known to one skilled in the art. Preferable doses (single administration) of bethanechol chloride are in the range of 1 mg to 50 mg, preferably 2 mg to 25 mg, and more preferably 3 mg to 9 mg. More than one administration may be given each day.

It may be advantageous to combine or co-administer a product of the invention with other classes of drug. Drugs which may be co-administered include, but are not limited to, acetylcholinesterase inhibitors.

The following Studies provide evidence for the utility of the present invention. Formulations 6, 9 and 14C illustrate the invention.

Study 1

Four formulations have been evaluated in rabbit salivary flow experiments. The formulations all contained 50 mg/ml bethanechol in slightly different mixed solvent systems. Formulation 2 was very similar to the formulation evaluated in the rat, in the Preclinical Study reported in WO2011/058366, except that the rat formulation was saturated and contained an excess of drug, whereas the four formulations used in this Study were clear solutions of drug below the saturation level. Their compositions are given in Table 1.

TABLE 1

| | | Formulation | | | |
|---|---|---|---|---|---|
| | | 2 | 6 | 9 | 14C |
| Component | Function | % w/w | | | |
| Bethanechol chloride | Active Pharmaceutical Ingredient | 5 | 5 | 5 | 5 |
| Phosphate buffer pH 5.4 | Buffer | 15 | 15 | | |
| Phosphate buffer pH 6.8 | Buffer | | | 15 | 15 |
| Glycerol | Carrier | 30 | 10 | 17.97 | 17.97 |
| Ethanol | Carrier | 20 | 20 | 20 | 20 |
| Macrogol 400 | Carrier | 29.97 | | 10 | 10 |
| Liquid maltitol (Lycasin ® 75/75 Maltitol Syrup) | Carrier | | 15 | 10 | 11.78 |
| Sorbitol solution | Carrier | | 15 | | |
| Dimethyl isosorbide | Carrier | | 20 | 20 | 20 |
| Carbomer (Carbopol 971P NF Polymer) | Viscosity modifier | | | 1 | 0.25 |
| Spearmint oil | Flavouring agent | | | 1 | |
| Sodium methyl paraben | Preservative | 0.018 | | 0.018 | |
| Sodium propyl paraben | Preservative | 0.02 | | 0.02 | |

More specifically, adult male New Zealand White rabbits, of approximate body weight 2.0 to 3 kg, were allocated in groups of three to be treated with formulations of bethanechol given in Table 1, designated 2, 6, 9 and 14C, along with each of their matching placebos. Animals were anaesthetised with urethane, administered IP, and heart rate was monitored via ECG leads. They were placed in the prone position after being anaesthetised (this inhibits the drug from entering the GI tract). Salivation was measured by inserting pre-weighed cotton wool balls into the oral cavity, removing after five or ten minutes and weighing. The difference in weight provided an estimate of salivary flow.

A series of baseline measurements was obtained prior to dosing. At time zero, vehicle formulations were applied as 2 equal aliquots totalling 100 μL to the oral mucosa on each side of the mouth. The placebo was left in the mouth for 5 minutes at which time the oral cavity was cleaned with a cotton wool ball which was then weighed. Serial salivary flow measurements were then taken for the next 60 minutes. At that time, active drug was applied by the same method as for placebo and salivary flow measured over the next 120 minutes. Efficacy data are shown in FIG. 1 (where the arrow at time 0 indicates the administration of the formulations containing bethanechol).

All formulations were significantly better than their respective vehicles in terms of overall salivary flow (p<0.001). In ranking terms, formulation 14C was superior to 9, which was superior to 6. Formulation 6 was markedly better than 2 over the first 60 minutes but thereafter was similar, so that over the entire 120 minutes there was not a statistically significant superiority. Average salivary flow rates (mg/min) are shown in Table 2. Vehicle data were highly consistent, suggesting good experimental technique.

TABLE 2

| Formulation | Vehicle | Active | % change |
|---|---|---|---|
| 2 | 5.44 | 12.03 | +221% |
| 6 | 4.26 | 17.76 | +417% |
| 9 | 4.79 | 25.55 | +533% |
| 14C | 5.65 | 36.14 | +640% |

Figure 2:
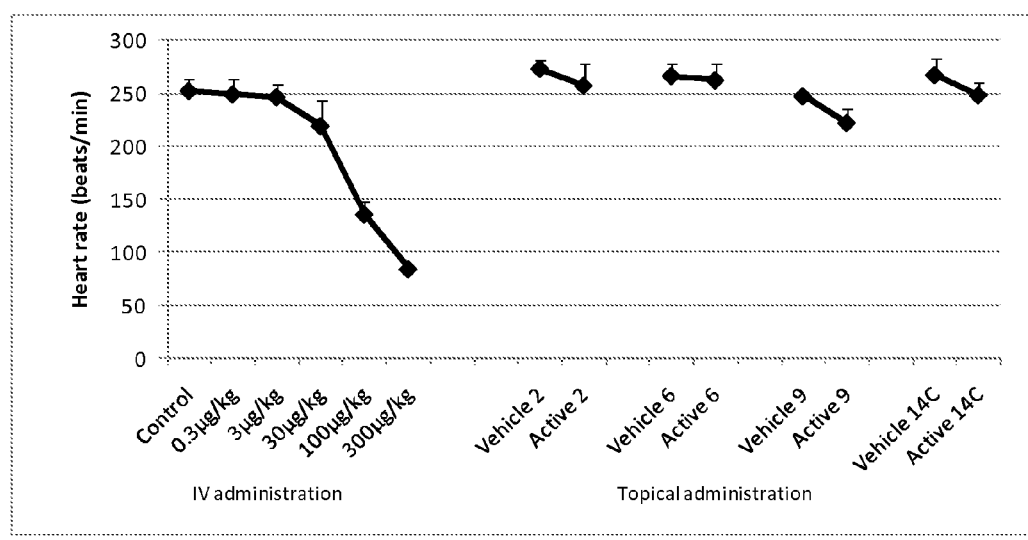
FIG. 2 is a plot of heart rate (beats/mins) with respect to various different administrations.

At the end of the experiment, one animal from each group was given bethanechol intravenously at a range of doses, in order to produce a dose-response curve for heart rate. This was compared to the effect of the active formulations, when given topically, on heart rate. Data are shown in FIG. 2.

None of the formulations of bethanechol, when applied oromucosally, had a significant effect on heart rate, whereas IV bethanechol caused a marked and dose-dependent bradycardia. This indicates that systemic absorption of bethanechol via the oral mucosa was minimal, using the formulations administered.

In a further, separate experiment, formulation 14C and its matching placebo were given to 3 anaesthetised rabbits in which blood pressure, via an indwelling cannula in the carotid artery, was monitored, along with heart rate. Administration of placebo or active (14C) into the buccal cavity (as described above) did not affect blood pressure or heart rate, whereas intravenous bethanechol chloride reduced blood pressure and heart rate, with clear dose-related effects at 30, 100 and 300 µg/kg.

Study 2

In a Phase 1 study involving four healthy volunteers, Formulation 14C applied topically to the oral mucosa at doses up to 20 mg, kept in situ for two minutes. This was well tolerated, with no significant adverse events. The same study demonstrated that the pharmacokinetics of oral and oromucosal bethanechol are linear.

This study also showed that the formulation, when applied to the oromucosal surface for two minutes, delivered small but measurable quantities of bethanechol into the systemic circulation, strongly suggestive of significant absorption into the mucosa of the oral cavity. This local absorption is likely to deliver enough bethanechol to the minor salivary glands, numbering in the hundreds to thousands and located immediately below the oral mucosa, to stimulate them to produce mucin-rich saliva which is disproportionately important for ensuring a comfortable month feel. When added to the salivary stimulation achieved by oral ingestion of bethanechol, it may reasonably be concluded that the formulation can produce better relief from xerostomia, with fewer side-effects, than purely systemic dosing of bethanechol.

Study 3

This study investigates bethanechol, applied oromucosally and subsequently ingested, in 30 cancer patients with xerostomia, a patient population with a significant unmet medical need. Subjects are randomised to receive either 20 mg bethanechol or matching placebo, in a double blind fashion, four times a day for one week. Study drug is applied by the patients to their oromucosal surface and left in situ for as long as possible, ideally at least two minutes. The mouth contents are swallowed, allowing systemic absorption of any unabsorbed study drug. After a one-week wash-out period, subjects return to receive the opposite treatment for one week.

A dose of 20 mg qds has been selected for this proof of concept study, based on Study 2. It is within the recommended range of oral bethanechol dosing in the Summary of Product Characteristics of the approved drug, which is 10-25 mg three or four times daily. This dose is therefore expected to carry negligible safety risk but should offer substantial efficacy benefits.

Substantial clinical experience with oral bethanechol points to a normal, positive dose-response for the agent in both its approved urinary and gastrointestinal indications and when used "off-label" to treat xerostomia. However, it is possible that the topical application of bethanechol may deliver much more bethanechol than is required to the minor salivary glands embedded in the oral mucosa. If that is the case, then a significantly lower dose than 20 mg might still deliver appreciable efficacy. Therefore, there is the option to enrol a second cohort of subjects at a significantly lower dose, such as 5 mg.

Two formulations were prepared, as shown in Tables 3 and 4. They are liquid formulations of bethanechol chloride intended for oromucosal and oral administration, in concentrations of 40 mg/mL and 50 mg/mL (expressed as the chloride).

The 40 mg/mL formulation is filled at a volume of 3 mL into a 15 mL type III amber glass bottle fitted with a PTFE-wadded tamper-evident polypropylene screw cap. The bottle may also be fitted with an indwelling LDPE syringe adapter. The composition of one bottle is presented in Table 3.

The 50 mg/mL formulation is filled at a volume of 10 mL into a 30 mL type III amber glass bottle fitted with a PTFE-wadded tamper-evident polypropylene screw cap. The composition of one bottle is presented in Table 4.

TABLE 3

| Component | Function | % v/w | Quantity (g) per bottle (nominal 3 mL fill) |
|---|---|---|---|
| Bethanechol chloride | Active Pharmaceutical Ingredient | 4 | 0.12 |
| Phosphate buffer pH 6.8* | pH Buffer | 15 | 0.45 |
| Glycerol | Carrier | 17.97 | 0.539 |
| Ethanol | Carrier | 20 | 0.60 |
| Macrogol 400 | Carrier | 10 | 0.30 |
| Dimethyl isosorbide | Carrier | 20 | 0.60 |
| Carbomer (Carbopol 971P NF Polymer) | Viscosity Modifier | 0.25 | 0.0075 |
| Liquid maltitol (Lycasin ® 75/75 Maltitol Syrup) | Carrier/ Sweetener | To 100 | To 3 mL |

*Each 0.45 g of phosphate buffer pH 6.8 contains 0.00306 g potassium dihydrogen orthophosphate and 0.00039 g sodium hydroxide in water for injection

TABLE 4

| Component | Function | % v/w | Quantity (g) per bottle (nominal 10 mL fill) |
|---|---|---|---|
| Bethanechol chloride | Active Pharmaceutical Ingredient | 5 | 0.50 |
| Phosphate buffer pH 6.8* | pH Buffer | 15 | 1.5 |
| Glycerol | Carrier | 17.97 | 1.797 |
| Ethanol | Carrier | 20 | 2.0 |
| Macrogol 400 | Carrier | 10 | 1.0 |

TABLE 4-continued

| Component | Function | % v/w | Quantity (g) per bottle (nominal 10 mL fill) |
|---|---|---|---|
| Dimethyl isosorbide | Carrier | 20 | 2.0 |
| Carbomer (Carbopol 971P NF Polymer) | Viscosity Modifier | 0.25 | 0.025 |
| Liquid maltitol (Lycasin ® 75/75 Maltitol Syrup) | Carrier/ Sweetener | To 100 | To 10 mL |

*Each 1.5 g of phosphate buffer pH 6.8 contains 0.0102 g potassium dihydrogen orthophosphate and 0.0013 g sodium hydroxide in water for injection The following process describes the manufacture of the 40 mg/mL and 50 mg/mL solutions.
1. Add 1123.13 g of glycerol and 937.5 g of pH 6.8 phosphate buffer (see below) to a 5 L vessel and mix for 10 minutes using a suitable overhead stirrer and paddle at a speed of 400 rpm.
2. Adjust the angle of the stirrer to approximately 60° and increase the stirrer speed to 700-900 rpm to create a vortex in the mixture from step 1. Sieve the carbomer through a 1000 pm sieve. Slowly add 15.625 g of sieved carbomer to the vortex over a 20 minute period, ensuring that time is allowed between each addition for the carbomer to wet before adding more.
3. After all the carbomer has been added mix for a further 45 minutes at 600 rpm to allow it to hydrate fully.
4. Homogenise for 30 minutes or until no particles of carbomer are evident.
5. Add 624 g Macrogol 400 and mix for a further 10 minutes at 500 rpm.
6. Add 1250 g ethanol and mix for 5 minutes at 500 rpm.
7. Add 1250 g dimethyl isosorbide and mix for 5 minutes at 500 rpm.
8. Sieve the bethanechol through a 1000 pm sieve and slowly add 250 g of the sieved active pharmaceutical ingredient to the mixture for the 400 mg/mL solution, or 312.5 g for the 50 mg/mL solution. After addition is complete, mix for a further 5 minutes at 500 rpm.
9. Make the mixture up to volume (6250 mL) with liquid maltitol and mix for a further 5 minutes at 500 rpm.
10. Measure the pH of the resultant formulation.
11. 3 mL of 40 mg/mL formulation are filled into 15 mL amber type III glass bottles fitted with a PTFE-wadded tamper-evident polypropylene screw cap and which may also be fitted with an indwelling LDPE syringe adapter. 10 mL of 50 mg/mL formulation are filled into 30 mL amber type III glass bottles fitted with a PTFE-wadded tamper-evident polypropylene screw cap. The bottles are labelled appropriately.

The buffer is prepared as follows:
1. Transfer 27.22 g of potassium dihydrogen orthophosphate to a 1000 mL volumetric flask and make up to volume with water for injection.
2. Transfer accurately 100 mL of 2M carbonate-free sodium hydroxide solution to a 1000 mL volumetric flask. Make up to volume with water for injection.
3. Transfer 500 mL of material from step 1 to a 5 L vessel, and add 224 mL of solution from step 2. Add approximately 1200 mL of water for injection and mix well. Adjust the pH to 6.8±0.05 using 85% orthophosphoric acid, then make up to volume (2000 mL) with water for injection.

The invention claimed is:

1. A buccal formulation comprising bethanechol and 5-40% (w/w) dimethyl isosorbide.
2. The formulation according to claim 1, further comprising a preservative.
3. The formulation according to claim 1, wherein the bethanechol is in the form of the chloride.
4. The formulation according to claim 1, wherein the formulation is a sub-saturated solution of bethanechol.
5. The formulation according to claim 1, wherein the formulation upon administration is maintained in the buccal cavity for a period of time prior to being swallowed.
6. The formulation according to claim 1, wherein the formulation is used in a method for the treatment of xerostomia.
7. The formulation according to claim 6, wherein the xerostomia is associated with head and neck cancer.
8. The formulation according to claim 6, wherein the xerostomia is associated with drug treatment.
9. The formulation according to claim 6, wherein the xerostomia is associated with cancer chemotherapy treatment.
10. The formulation according to claim 6, wherein the xerostomia is associated with Sjorgren's syndrome.
11. The formulation according to claim 6, wherein the xerostomia is associated with late-stage cancer.
12. A method for treating xerostomia, comprising buccal administration of bethanechol in combination with 5-40% (w/w) dimethyl isosorbide to a subject in need thereof, wherein the bethanechol upon administration is maintained in the buccal cavity for a period of time prior to being swallowed.
13. The method according to claim 12, wherein the bethanechol is in the form of the chloride.
14. The method according to claim 12, wherein the bethanechol is maintained in the buccal cavity from 30 seconds to 5 minutes prior to being swallowed.
15. The method according to claim 12, wherein the xerostomia is associated with head and neck cancer.
16. The method according to claim 12, wherein the xerostomia is associated with drug treatment.
17. The method according to claim 12, wherein the xerostomia is associated with cancer chemotherapy treatment.
18. The method according to claim 12, wherein the xerostomia is associated with Sjorgren's syndrome.
19. The method according to claim 12, wherein the xerostomia is associated with late-stage cancer.

* * * * *